May 10, 1955 R. L. BYRUM Plant Pat. 1,391
ROSE PLANT
Filed Oct. 1, 1954
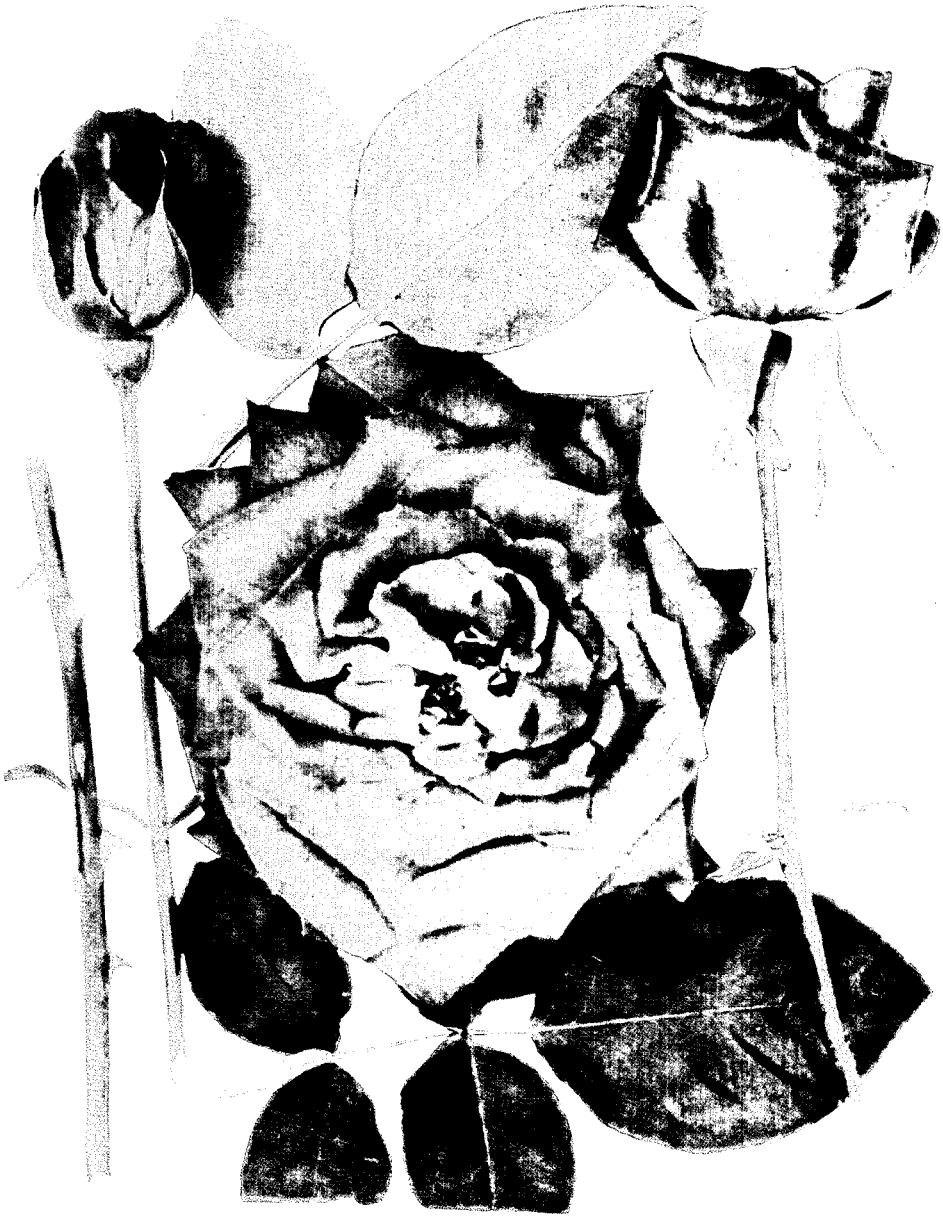
Inventor.
R. L. Byrum
By: Robb & Robb
attorneys.

United States Patent Office

Plant Pat. 1,391
Patented May 10, 1955

1,391

ROSE PLANT

Roy L. Byrum, Richmond, Ind., assignor to Joseph H. Hill Company, Richmond, Ind., a corporation of Indiana Application October 1, 1954, Serial No. 459,875

1 Claim. (Cl. 47—61)

The present invention relates to a new and distinct variety of rose plant of the hybrid tea class, which was originated by me by crossing the variety "Hill Crest" (Plant Patent No. 844) with the variety "Sister Kenny" (Plant Patent No. 1146).

The primary objective in making this cross was to obtain a new variety of red rose which is better for winter forcing, and which combines the best characteristics of the parent varieties. This objective was fully achieved, as evidenced by the fact that my new variety is particularly characterized by the following outstanding features:

(1) Better freedom of growth under winter forcing conditions;

(2) Produces cut flowers of better quality with better shipping qualities than any truly Red rose of which I am aware; and (3) Greater profusion of flowers.

As compared with its seed parent, "Hill Crest," the buds of my new variety have a better shape at the cutting stage, and have better keeping and shipping qualities, along with a clearer color, whereas in comparison with its pollen parent, "Sister Kenny," my new variety is a much better cut flower forcer under glass, since this latter parent variety is primarily suited for growing out-of-doors and is too single for greenhouse cut flower forcing.

The foregoing characteristics and distinctions definitely differentiate my new variety from its parents, as well as from all other varieties of which I am aware, and asexual reproduction of my new variety by grafting, as performed at Richmond, Indiana, and by budding, as performed at Wills Point, Texas, shows that the foregoing characteristics and distinctions come true to form and are established and transmitted through succeeding propagations.

The accompaning drawing shows typical specimens of the flowers, foliage and stems of my new variety in different stages of development and as depicted in color as nearly true as it is reasonably possible to make the same in a color illustration of this character.

The following is a detailed description of my new variety, with color terminology in accordance with Ridgway's Color Standards and Nomenclature (hereinafter abbreviated as "Ridgway"), Koster's Color Guide (hereinafter abbreviated as "Koster") and Robert F. Wilson's Horticultural Colour Chart (hereinafter abbreviated as "Wilson"), as indicated:

Type: Greenhouse; bush; seedling.
Class: Hybrid tea.
Breeding: Seedling.
*Seed parent.*—"Hill Crest."
*Pollen parent.*—"Sister Kenny."
Propagation: Holds its distinguishing characteristics through succeeding propagations by both grafting and budding.

FLOWER

Locality where grown and observed: Richmond, Indiana, and Wills Point, Texas.

Flowers borne: 1 to stem; on strong stems of medium length.
Quantity of bloom: Abundant.
Continuity: Continuous.
Fragrance: Slight. Nature—tea.
Bud:
*Peduncle.*—Strong; erect. Length—medium. Diameter—medium. Bark—slightly rough. Color—Parsley Green, Plate 00962/3 (Wilson). Thorns—none. Prickles—few. Color—Rhodonite Red, Plate 0022/3 (Wilson). Hairs—few. Color—Rhodonite Red, Plate 0022/3 (Wilson).
*Before calyx breaks.*—Size—medium large. Form—short pointed; ovoid; with a conspicuous neck; with foliaceous appendages on the surface of the bud; with mostly slender, but a few stout, slightly cut foliaceous parts extending beyond the tip of the bud equal to ¼ or more of its length. Color—Spinach Green, Plate 0960/3 (Wilson).
*As calyx breaks.*—Color (outside of petal)—Cardinal Red, Plate 822/3 (Wilson).
*As first petal opens.*—Size—medium large. Form—short pointed; ovoid. Color: outside—Cardinal Red, Plate 822/3 (Wilson), pencilled lightly with Cardinal Red, Plate 822 (Wilson); inside—Currant Red, Plate 821/3 (Wilson), overlaid with a velvety red sheen.
*Opening.*—Opens up well in greenhouse; is normally affected by weather, but has no unusual characteristics.
Bloom:
*Size (when fully open).*—Large; from 3½ inches to 4½ inches.
*Petalage.*—Double, but stamens not hidden; from 40 to 45 petals; arranged irregularly.
*Form.*—Full and high-centered at first, but becoming open; petals being at first tightly rolled outward, but becoming loosely rolled outward later at maturity.
Petals: Thick; leathery. Inside—velvety. Outside—satiny.
*Shape.*—Outside petals—obovate; apex retuse. Intermediate petals—obovate; apex obtuse. Inside petals—obovate; apex obtuse.

This description of a newly opened flower was made from a rose grown in a greenhouse in the month of May, at Richmond, Indiana:

Color:
*Outside petal.*—Outside surface—Carmine, Plate I (Ridgway). Inside surface—Currant Red, Plate 821/3 (Wilson), overlaid with a velvety sheen of near Cardinal Red, Plate 822/2 (Wilson); some petals have a white stripe in center.
*Intermediate petal.*—Outside surface—Carmine, Plate I (Ridgway). Inside surface—Currant Red, Plate 821/3 (Wilson), overlaid with a velvety sheen of near Cardinal Red, Plate 822/2 (Wilson).
*Inner petal.*—Outside surface—Carmine, Plate I (Ridgway). Inside surface—Currant Red, Plate 821/3 (Wilson), overlaid with a velvety sheen of Cardinal Red, Plate 822/3 (Wilson).

This description was made from a rose that was open for three days in a greenhouse in the month of June, at Richmond, Indiana:

Color:
*Outside petal.*—Outside surface—Rose Red, Plate 724/2 (Wilson). Inside surface—Rose Red, Plate 724 (Wilson).
*Intermediate petal.*—Outside surface—Rose Red, Plate 724/2 (Wilson). Inside surface—Rose Red, Plate 724 (Wilson).

*Inner petal.*—Outside surface—Rose Red, Plate 724/2 (Wilson); some petals have a streak of white in center. Inside surface—Rose Red, Plate 724 (Wilson).

Behavior: Persist; affected normally by weather conditions, without unusual characteristics, but fade to Rose Red, Plate 724/3 (Wilson).

Flower longevity: Cut flowers grown in greenhouse and kept at living-room temperatures—4 or 5 days in May.

General color effect of open bloom:

*Newly opened flower.*—Currant Red, Plate 821/3 (Wilson).

*3-days open.*—Cardinal Red, Plate 822/3 (Wilson).

PLANT

Foliage:

*Leaves.*—Compound of 5 leaflets; abundant; medium large size; heavy; semi-glossy; wrinkled.

*Leaflets.*—Shape—ovoid. Apex—acute. Base—round. Margin—simply serrate.

*Color.*—Mature: upper surface—between Spinach Green, Plate 0960 (Wilson) and Taxus Green, Plate 81 (Koster); under surface—Cedar Green, Plate 80 (Koster). Young: upper surface—Pod Green, Plate 061/3 (Wilson), overlaid with near Vandyke Red, Plate XIII (Ridgway); under surface—Pod Green, Plate 061/3 (Wilson), overlaid with near Vandyke Red, Plate XIII (Ridgway).

*Rachis (the supporting stem of the compound leaf).*—Medium heavy. Upper side—grooved. Under side—Prickly.

*Stipules.*—Moderately long; narrow; with moderately short points turning out at an angle of more than 45°.

Growth:

*Habit.*—Bush; upright; much-branched.

*Growth.*—Vigorous.

*Canes.*—Medium diameter.

*Main stems.*—Color—Spinach Green, Plate 0960/3 (Wilson, partly overlaid with Maroon, Plate 97 (Koster) ). Thorns—several; medium length; hooked downward; with long base. Color—Van Dyck Brown, Plate 96 (Koster). Prickles—several. Color—Van Dyck Brown, Plate 96 (Koster). Hairs—none.

*Branches.*—Color—near Sage Green, Plate 78 (Koster). Thorns—several; medium length; hooked downward; with long base. Color—Uranium Green, Plate 63/3 (Wilson) at point (tip), gradually changing through Spinel Red, Plate 0023/3 (Wilson) to Spinel Red, Plate 0023/2 (Wilson). Prickles—none. Hairs—none.

*New shoots.*—Color—Scheele's Green, Plate 860/3 (Wilson). Thorns—several; medium length; hooked downward; with long base. Color—near Lilac, Plate 48 (Koster). Prickles—several. Color—near Lilac, Plate 48 (Koster). Hairs—none.

REPRODUCTIVE ORGANS

Stamens: Many; arranged regularly about pistils.

Filaments: Medium length; most with anthers. Color—Spinel Red, Plate 0023/1 (Wilson).

Anthers: Medium small; all open at once. Color—Pure Black, Plate 98 (Koster).

Pollen: Abundant. Color—Yellow Cadmium, Plate 9 (Koster).

Pistils: Many.

Styles: Uneven length; medium length; moderately thin; bunched. Color—Cardinal Red, Plate 822/3 (Wilson).

Stigma: Color—Pure White, Plate 1 (Koster).

Ovularies: Some protruding from calyx.

Hips: Medium length; obovate; with inconspicuous neck; pear-shaped; very smooth; walls thick and fleshy. Color (when ripe)—near Lemon Yellow, Plate 7 (Koster).

Sepals: Permanent; medium length; spear-shaped. Color: inside—Spinach Green, Plate 75 (Koster), overlaid with white fuzz; outside—Spinach Green, Plate 75 (Koster).

Seeds: Many; medium large.

I claim:

A new and distinct variety of rose plant of the hybrid tea class, substantially as herein shown and described, characterized particularly as to novelty by its improved freedom of growth under winter forcing conditions, the improved keeping and shipping qualities of its cut flowers, the improved shape of its buds at the cutting stage, and the distinctive clear color of its flowers.

No references cited.